(12) United States Patent
Lucisano et al.

(10) Patent No.: US 10,041,897 B2
(45) Date of Patent: *Aug. 7, 2018

(54) HERMETIC IMPLANTABLE SENSOR

(75) Inventors: Joseph Y. Lucisano, SanDiego, CA (US); Mark B. Catlin, San Diego, CA (US)

(73) Assignee: Glysens, Incorporated, a California Corporation, San Diego, CA (US)

( * ) Notice: Subject to any disclaimer, the term of this patent is extended or adjusted under 35 U.S.C. 154(b) by 1100 days.

This patent is subject to a terminal disclaimer.

(21) Appl. No.: 13/024,209

(22) Filed: Feb. 9, 2011

(65) Prior Publication Data

US 2011/0137142 A1 Jun. 9, 2011

Related U.S. Application Data

(63) Continuation of application No. 10/925,074, filed on Aug. 23, 2004, now Pat. No. 7,894,870, which is a continuation of application No. 10/778,863, filed on Feb. 13, 2004, now abandoned.

(51) Int. Cl.
  *A61B 5/05* (2006.01)
  *G01N 27/12* (2006.01)
  *A61B 5/145* (2006.01)
  *A61B 5/1486* (2006.01)

(52) U.S. Cl.
  CPC .......... *G01N 27/12* (2013.01); *A61B 5/14532* (2013.01); *A61B 5/14865* (2013.01); *A61B 2562/12* (2013.01)

(58) Field of Classification Search
  USPC .................................................. 600/345, 347
  See application file for complete search history.

(56) References Cited

U.S. PATENT DOCUMENTS

| | | |
|---|---|---|
| 3,099,575 A | 7/1963 | Hill |
| 4,484,987 A | 11/1984 | Gough |
| 4,650,547 A | 3/1987 | Gough |
| 4,703,756 A | 11/1987 | Gough et al. |
| 4,890,620 A | 1/1990 | Gough |
| 5,560,098 A | 10/1996 | Robins |
| 5,750,926 A | 5/1998 | Schulman |
| 5,782,891 A | 7/1998 | Hassler et al. |
| 5,887,240 A | 3/1999 | Fournier |
| 5,985,129 A | 11/1999 | Gough |
| 6,516,808 B2 | 2/2003 | Schulman |

(Continued)

OTHER PUBLICATIONS

Alarez-Icaza and Bilitewski, "Mass Production of Biosensors," *Anal. Chem.* (1993) 65(11):525-533.
Bilitewski et al., "Glucose Biosensors Based on Thick Film Technology," *Biosens. Bioelectron.* (1991) 6:369-373, Elsevier Science Publishers Ltd. England.

(Continued)

*Primary Examiner* — Etsub Berhanu
(74) *Attorney, Agent, or Firm* — DLA Piper LLP (US)

(57) ABSTRACT

At least one conductor is formed at a preselected location on a substrate made of a first insulating material having a high temperature resistance. The conductor is made from a solidified electrically conductive thick film material. A coating made of a second insulating material is formed over the substrate to hermetically seal at least a portion of the conductor. An exposed distal region of the conductor provides a detection electrode. The conductor has a reduced porosity that inhibits migration of fluid or constituents thereof through the conductor.

18 Claims, 6 Drawing Sheets

(56) References Cited

U.S. PATENT DOCUMENTS

| | | |
|---|---|---|
| 6,721,587 B2 | 4/2004 | Gough |
| 7,189,341 B2 | 3/2007 | Li |
| 7,514,791 B2 | 4/2009 | Shah |
| 2003/0049166 A1* | 3/2003 | Pendo et al. ............... 422/56 |
| 2003/0053784 A1* | 3/2003 | LaBrake ............... C03C 17/22 385/128 |
| 2003/0179167 A1* | 9/2003 | Kolluri ............... G09F 9/372 345/85 |
| 2003/0181794 A1* | 9/2003 | Rini ............... A61B 5/0031 600/300 |
| 2004/0057043 A1* | 3/2004 | Newman ............... G01M 3/363 356/237.1 |
| 2004/0190111 A1* | 9/2004 | Callies ............... G02B 26/0833 359/291 |

OTHER PUBLICATIONS

Cha et al., "Electrochemical Behavior of Microfabricated Thick-Film Electrodes," *Sensors and Actuators B* (1990), 2:277-281, Elsevier Sequoia, The Netherlands.

Dutronc et al., "Influences of the Nature of the Screen-Printed Electrode Metal on the Transport and Detection Properties of Thick-Film Semiconductor Gas Sensors," *Sensors and Actuators B* (1992), 6:279-284, Elsevier Sequoia.

Golonka et al., "The Influence of the Electrode Material on the Sensitivity of an $SnO_2$ Thick-Film Gas Sensor," *Sensors and Actuators B*. (1994), 18-19:453-456, Elsevier Sequoia.

Holc and Hrovat, "Interaction between Thick-Film Platinum Electrodes and yttria-Stabilized $ZrO_2$ Ceramic," *J. Mater. Sci. Letters* (1989), 8:635-637.

Holmes and Loasby, *Handbook of Thick Film Technology* (1976), 14-73, Electrochemical Publications Limited.

* cited by examiner

HERMETIC IMPLANTABLE SENSOR

CROSS REFERENCE TO RELATED APPLICATION

This application is a continuation application of U.S. application Ser. No. 10/925,074 filed Aug. 23, 2004, now pending; which is a continuation application Ser. No. 10/778,863 filed Feb. 13, 2004, now abandoned. The disclosure of each of the prior applications is considered part of and is incorporated by reference in the disclosure of this application.

BACKGROUND OF THE INVENTION

Field of the Invention

The present invention relates to probes, sensors, stimulators, antennas, and other electrical and electronic devices that can be inserted into the human body or other biological environment, and more particularly, to an improved hermetic construction for the electrical conductors of such devices that results in minimal instances of failure and/or inaccuracy during implanted or submerged operation.

Background Information

Implantable sensors for monitoring biological agents in the human body have been under development for many years. One example is the glucose sensor that promises to provide diabetics with improved monitoring of blood sugar levels to thereby tailor insulin treatment to alleviate the symptoms and long-term damaging effects of diabetes mellitus. In one form, an implantable electrochemical glucose sensor utilizes an enzyme such as glucose oxidase (GO) to catalytically convert glucose to gluconic acid with the simultaneous consumption of oxygen, which is detected with amperometric (current measuring) electrodes. Such electrodes are commonly fabricated from the platinum-family noble metals, because of such metals' catalytic properties and resistance to corrosion. See, for example, U.S. Pat. No. 4,890,620 granted Jan. 2, 1990 to David A. Gough, the entire disclosure of which is hereby incorporated by reference.

There are many technical challenges in designing a commercially viable implantable sensor that will meet medical device regulatory and performance requirements. First and foremost it must be safe, accurate and reliable. An implantable sensor should also be compact and be entirely contained within the body, i.e. it should not require any wires or other structures to extend through the skin, which would be unsightly, uncomfortable and a continuing source of infection. Biocompatible materials must be used where portions of the sensor come into physical contact with the body. Fabrication techniques developed in the micro-electronics industry along with specialized electrode energization and signal processing techniques offer the potential to solve many of these problems, however, failures and inaccuracies associated with the electrodes and associated structures have been problematic. In particular, there have been problems in designing and mounting the electrodes, and the electrically conductive structures to which they are connected, in a manner that will allow a hermetic seal that prevents signal degradation, shorts and other failures.

U.S. Pat. No. 6,516,808 granted to Joseph H. Schulman discloses a hermetic feedthrough for an implantable substrate sensor that comprises electronic circuitry formed within, or on, a substrate. A protective coating covers the substrate, forming a hermetically sealed package having the circuitry under the coating. The circuitry has electrically conductive pads for communicating and/or providing power to the circuitry. Electrical pathways provide hermetic electrical connection to the conductive pads for external connection to the sealed circuitry. In one embodiment, the pathway is a via that is made from a biocompatible material that is made hermetic by either increasing its thickness or by ion beam deposition. Alternatively, the pathways are formed from metal traces, surrounded by a biocompatible insulation material, essentially parallel to the surface of the substrate that are connected to the conductive pads by first vias and have second ends externally accessible to the sealed package to provide external electrical connection to the hermetically sealed circuitry within. The aforementioned structures of U.S. Pat. No. 6,516,808 of Schulman are complex and expensive to fabricate.

SUMMARY OF THE INVENTION

It is therefore the primary object of the present invention to provide an improved hermetic construction for the electrical conductors of implantable or submersible devices, both medical and non-medical, including the conductors that lead to, or form, the detection electrodes of implantable sensors, that results in minimal instances of failure and/or inaccuracy during implanted operation.

According to the present invention, a sensor comprises a substrate made of a first insulating material having a high temperature resistance. At least one conductor is formed at a preselected location on the substrate and is made from a solidified electrically conductive thick film material. A coating made of a second insulating material is formed over the substrate to hermetically seal at least a portion of the conductor. An exposed distal region of the conductor provides a detection electrode. The conductor has a reduced porosity that inhibits migration of fluid or constituents thereof through the conductor.

The present invention also provides a method of fabricating a sensor. According to an initial step of the method, a substrate made of a first insulating material is provided that has a high temperature resistance. Next, an electrically conductive thick film material is deposited on the substrate to form at least one un-solidified conductor. The electrically conductive thick film material is then heated to a first predetermined temperature, below a second predetermined melting temperature thereof, which is sufficient to sinter a plurality of metal particles in the electrically conductive thick film material. The thick film material is allowed to cool to produce at least one solidified conductor having a porosity that is sufficiently low such that it may become hermetic when coated. A portion of the conductor is coated with a second insulating material leaving at least one exposed region that provides a detection electrode.

DETAILED DESCRIPTION OF THE INVENTION

Figures 1, 2, 3:
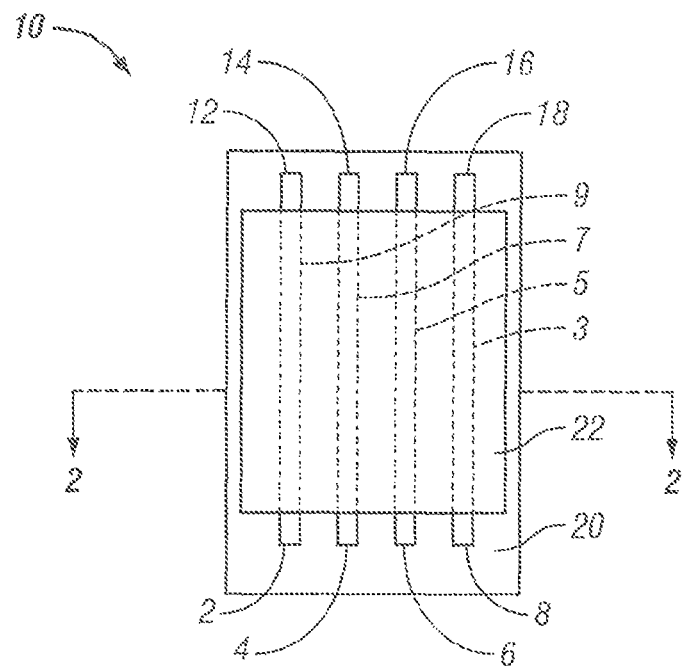
FIG. 1 is a diagrammatic plan view of an embodiment of a sensor intended for in vitro use.
FIG. 2 is a cross-sectional view of the in vitro sensor of FIG. 1 which is taken along line 2-2 of FIG. 1.
FIG. 3 is a cross-sectional view similar to FIG. 2 illustrating a slightly modified version of the in vitro sensor of FIG. 1.

FIG. 1 illustrates an embodiment of the invention in the form of an in vitro electrochemical sensor 10 that is suitable for monitoring the level of a biological agent such as glucose, lactate, cholesterol, etc. in an aqueous solution. The sensor 10 has the shape of a small credit card and one end thereof may be immersed in a body of fluid in a beaker or other container with the sensor 10 standing or being supported upright with its longer dimension extending vertically. The sensor 10 includes spaced-apart elongate parallel electrical conductors, 3, 5, 7 and 9. One distal end of each of the aforementioned conductors serves as a detection electrode, thus providing detection electrodes 2, 4, 6 and 8. The other, proximal end of each one of the aforementioned conductors serves as a contact pad, thus providing contact pads 12, 14, 16 and 18. In addition to the elongate parallel conductors, 3, 5, 7 and 9, the sensor 10 may also have at least one insulation-testing conductor (not illustrated), which is also made of the same thick film material. The glass coating hermetically seals an entire portion of the insulation-testing conductor that would otherwise come into contact with the bodily fluid. The circuit can use the insulation-testing conductor for testing for shorts underneath, and breaks in, the insulating coating.

The electrical conductors 3, 5, 7 and 9 are formed at preselected locations on a rigid high temperature resistant inert material in the form of a planar rectangular piece of ceramic substrate 20. Suitable substrates include AD-96 and AD-995 alumina ceramic available from CoorsTek. The electrical conductors 3, 5, 7 and 9 are made by screening or otherwise depositing an electrically conductive thick film material preferably in the form of a paste made primarily of platinum particles and an organic carrier or vehicle. Suitable electrically conductive thick film materials include VITR-AU-LESS® 4082 and CONDUCTROX® 3804, both commercially available from Ferro Electronic Materials. The term "thick film" refers to materials such as pastes, inks and the like applied by screening or other mechanical means used to form conductors, traces, pads, layers etc. having thicknesses typically measured in thousandths of an inch, or fractions thereof. By way of comparison, the term "thin film" normally refers to materials deposited via sputtering, vapor deposition, ion beam deposition, etc. in order to form layers having thicknesses typically measured in terms of microns or fractions of microns. The significant differences between thick film and thin film methods lie beyond the difference in thickness of the films produced by the methods. Thin film methods require costly, specialized equipment and also, because the films are thin, they require exquisite control of particulate contamination during the process in order to achieve acceptable film quality. By contrast, thick film methods utilize lower cost equipment and are less sensitive to contaminants. Thin film methods are capable of achieving finer geometries than thick film methods, but that capability is not required for producing many types of implantable medical devices.

In the various embodiments of the present invention described herein, thick film pastes are preferably applied by screen printing using conventional techniques well known in the art. As will be clear to persons skilled in the art, techniques alternative to screen printing, such as pad printing, roll printing, brushing, spraying, or dipping could also be employed to fabricate the devices described herein, depending on the geometries of the particular patterns required. Additionally, secondary patterning techniques, such as photolithography using photomasks and thick film pastes containing photo-sensitive compounds, as well as mechanical, hydraulic, or laser-based ablation techniques could be employed to generate particular patterns in the thick-film materials.

After the electrically conductive thick film material has been deposited on the substrate 20, it is dried in an oven and then heated in a furnace, or by other conventional means, to a temperature close to, but below, the melting point of the platinum. This sinters the platinum particles together to a high degree so that after they have cooled and solidified, the resulting electrical conductors, 3, 5, 7 and 9 have a reduced porosity which is significantly less than that which would otherwise result if the metal particles were heated to temperatures recommended by the thick film material manufacturers or those found in the prior art. Because of its collapsed geometry, particulate platinum that is processed at high temperatures traps little or no air (nor any other fluid that may expand when heated) when coated with a relatively viscous material such as glass or other thick film dielectric (insulating) material. This lack of porosity inhibits migration of fluid via capillary action, as well as gaseous diffusion, through the electrical conductors, 3, 5, 7 and 9. This fluid migration and/or gaseous diffusion can result in the buildup of salts and/or corrosion at the proximal ends of the conductors (contact pads 12, 14, 16 and 18) which can lead to sensor failure and/or inaccuracy. The lack of porosity also inhibits the formation of bubbles that may otherwise form in the overlying insulating layer while it is being fired or cured, said bubbles tending to disrupt hermeticity.

In order to form a collapsed layer of platinum in each of the electrical conductors, 3, 5, 7 and 9, the electrically conductive thick film is applied to the ceramic substrate 20 and fired in a furnace, preferably reaching a peak temperature between about 1600 degrees C. and about 1700 degrees C. The procedure has been successful at peak temperatures as low as 1500 degrees C. Lower peak temperatures require longer dwell times, i.e. the time during which the thick film is maintained at the peak temperature, which may be undesirable since it increases process time. Higher temperatures are also more energy intensive and tend to impact negatively on the substrate as well as on furniture that may be used in the furnace to aid in firing the substrate. Various dwell times may be employed to collapse the platinum particles depending upon their size and geometry, and the peak temperature. Dwell times between about ten minutes and about sixty minutes have produced good results. Various ramp rates may be used to achieve the peak temperature and the subsequent return to ambient temperature. Thermal shock resistance of the substrate 20 may dictate some maximum ramp rate. Ramp rates of about five degrees C. to about twenty degrees C. per minute have been found to be satisfactory using both alumina and zirconia substrates. Slower ramp rates could also be employed to similar effect, but require more furnace time and energy.

A coating 22 (FIG. 1) made of an inert insulating material such as glass is formed over the substrate 20 to hermetically seal the electrical conductors, 3, 5, 7 and 9, leaving exposed distal regions that provide the detection electrodes 2, 4, 6 and 8, and exposed proximal regions that provide contact pads, 12, 14, 16 and 18. The detection electrodes 2, 4, 6 and 8 are provided for contacting the fluid and the contact pads 12, 14, 16 and 18 are provided for making electrical connections to other circuitry.

Other substrate materials may be used such as oxides, carbides, borides, nitrides, and silicides of aluminum, zirconium, beryllium, silicon, titanium, yttrium, and zinc and mixtures thereof. It is important, however, that a high temperature resistant material be used for the substrate 20 since it must maintain its physical integrity when the electrically conductive thick film is deposited thereon and heated to a high temperature necessary for the high degree of sintering of the present invention. The electrically conductive thick film material may contain particles of a biocompatible metal such as platinum, palladium, rhodium, ruthenium, iridium and osmium. These metals are advantageously employed because they have high corrosion resistance and, for certain electrochemical sensor applications, catalytic properties. The electrochemical properties of the platinum-family noble metals are particularly useful in a hermetic sensor fabricated in accordance with our invention that utilizes glucose oxidase to catalytically convert glucose to gluconic acid with the simultaneous consumption of oxygen which is detected with amperometric (current measuring) electrodes. In general, it is necessary to heat the electrically conductive thick film material to a temperature within a range that extends from just below its melting point to approximately three hundred degrees C. below its melting point.

Referring to FIG. 2, the glass coating 22 may simultaneously bridge all the electrical conductors, 3, 5, 7 and 9. Alternatively, each of the electrical conductors, 3, 5, 7 and 9, may be coated with a separate discrete coating 22' as illustrated in FIG. 3. The distal or remote ends of the conductors 3, 5, 7 and 9 at the bottom of FIG. 1, that provide the detection electrodes, 2, 4, 6 and 8, are dipped into the liquid containing the substance or compound whose presence and/or level is to be detected. The proximal or near ends of the conductors 3, 5, 7 and 9 at the top of FIG. 1, that provide the contact pads, 12, 14, 16 and 18, are connected to suitable electronic instrumentation via clips (not illustrated) or other suitable means for sending and receiving the electrical signals as necessary for the sensor 10 to function as an electrochemical sensor. Suitable instrumentation includes the VMP potentiostat available from Bio-Logic Science Instrument SA. In some configurations, one or more of the detection electrodes may be coated, using conventional electroplating techniques, with another metal, such as silver, to form a reference electrode. A proximal portion of each of the electrical conductors, 3, 5, 7 and 9, could be configured for removably receiving a connector (not shown) attached to wires that lead to the driving and sensing circuitry (not shown).

The insulating glass coating 22 is normally applied over the electrical conductors, 3, 5, 7 and 9, after they have been sintered. Suitable glasses include ESL 4612-C, available from Electro-Science Laboratories, Inc. Various inert thick film glass and ceramic insulating materials may be used such as oxides, carbides, borides, nitrides, and silicides of aluminum, zirconium, beryllium, silicon, titanium, yttrium, and zinc and mixtures thereof. Each typically has a firing temperature well below the melting point of the metal particles in the electrically conductive thick film material from which the electrical conductors, 3, 5, 7 and 9, are formed.

Figure 4:
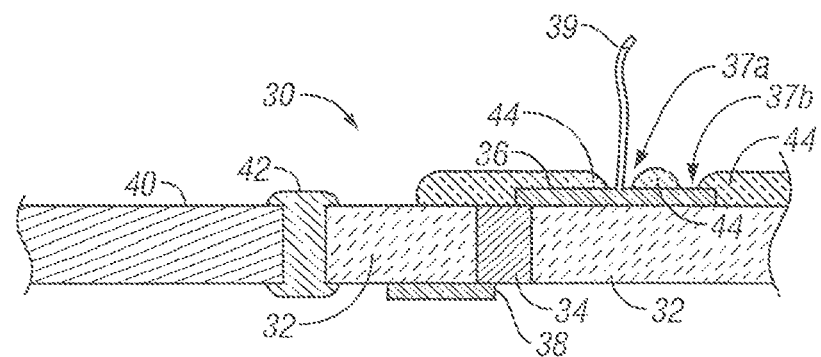
FIG. 4 is a greatly enlarged diagrammatic fragmentary cross-sectional view of an embodiment of a sensor intended for in vivo use.

FIG. 4 is a greatly enlarged diagrammatic fragmentary cross-sectional view of an embodiment 30 of our invention intended for in vivo use. A ceramic substrate 32 has a conductive filled via 34 that provides an interconnection means between a first conductor 36 formed on the exterior side of the substrate 32 and a second conductor 38 formed on the inside surface of the substrate 32. A metal case 40 surrounds circuitry (not illustrated) located beneath the ceramic substrate 32 and the metal case is hermetically sealed to substrate 32 via suitable means such as brazing 42. The circuitry may comprise various active and passive components, printed circuit boards, analog and digital components, transducers and batteries. The circuitry can be electrically connected to the second conductor 38 via wire bonding or other means so that the circuitry can energize and/or receive signals from the first conductor 36 through the conductive filled via 34. The conductive filled via 34 can be formed in a hole in the ceramic substrate 32 by screen printing a conductive thick film material or by inserting a wire, rivet, or other metallic element since it is coated with glass insulating layer 44 and therefore need not of itself provide a hermetic seal. The insulating layer 44 has at least one break to expose at least one region of the first conductor 36. In FIG. 4, two breaks are illustrated for convenience as 37a and 37b, although only one break may be required. The break 37a may be used to provide a connection location for a remote electrode such as a wire 39 that extends some distance, as would be used in a pacemaker, defibrillator, cochlear stimulator, neural stimulator or muscular stimulator. Alternatively, the break 37b may allow use of an exposed area of first conductor 36 as a detection electrode. The first conductor 36 is made from a thick film material including platinum particles that has been fired to sinter the particles and reduce the porosity thereof as previously explained. Platinum is advantageously employed in this embodiment because it tolerates high temperatures associated with brazing.

The metal case 40 may alternatively extend around the upper side of the substrate 32 in FIG. 4 so that the first conductor 36 is completely enclosed and the lower exposed end of the conductive filled via 34 functions as the detection electrode. Of course in this configuration, the lower exposed end of conductive filled via 34 may be used to provide a connection location for a remote electrode, such as a wire that extends some distance, as would be used in a pacemaker, defibrillator, cochlear stimulator, neural stimulator or muscular stimulator, similar to wire 39 and break 37a. Liquid and/or gas may migrate between the periphery of the conductive filled via 34 and the walls of the substrate 32 that form the aperture in which the conductive via 34 is formed, but the reduced porosity first conductor 36 advantageously prevents fluid or constituents thereof from migrating further along the first conductor 36 to any other components housed within the metal case 40 where they might otherwise cause device failures due to corrosion, the creation of an open circuit and/or shorting. Thus the advantages of our invention extend not only to electrodes formed of thick film materials which are fabricated to achieve reduced porosity, but to conductors within implantable devices that do not themselves directly contact fluid but may indirectly come into contact with same. In our currently preferred embodiment, the second conductor 38 functions as an extension of the electrode formed by the conductive filled via 34, but is otherwise optional. The wire 39 is optional.

Figure 5:
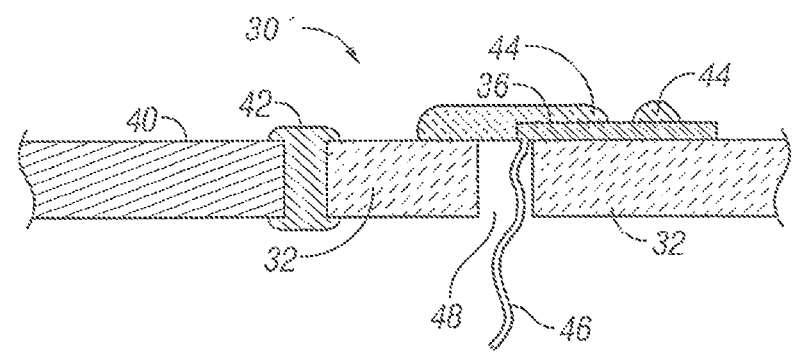
FIG. 5 is a view similar to FIG. 4 illustrating a slightly modified view of the in vivo sensor of FIG. 4.

FIG. 5 illustrates a slightly modified in vivo sensor 30' which is similar to the sensor 30 of FIG. 4 except that in the former an electrical connection between the circuitry within the metal case 40 is connected to the first conductor 36 via wire 46 that extends through a hollow void or through hole 48 in the substrate 32. A proximal portion of the first conductor 36 is preferably formed to allow electrical contact with a connector such as the conductive filled via 34 or wire 46. As illustrated in FIG. 4, the proximal end of the first conductor 36 overlaps the conductive filled via and is bonded thereto. The distal end of the first conductor 36 is exposed and may form a detection electrode.

Figure 6:
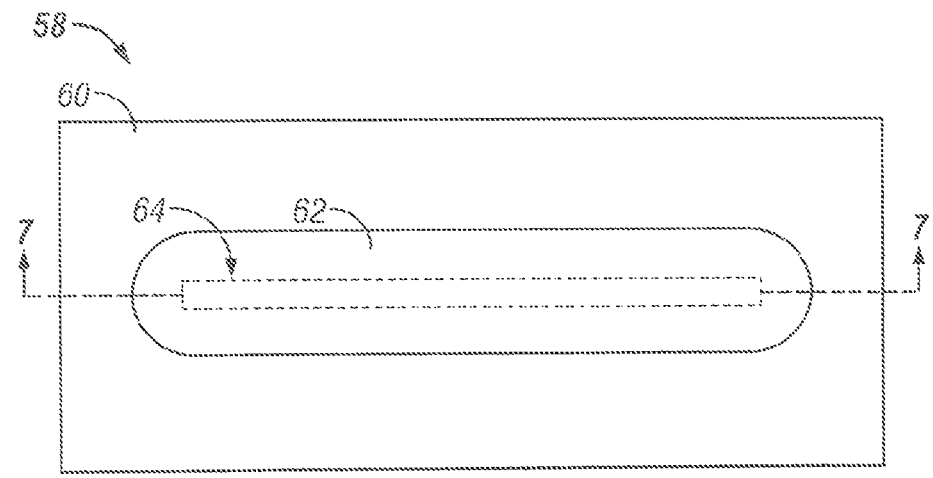
FIG. 6 is a diagrammatic plan view of a radio frequency antenna, intended for incorporation into an implantable device.

FIG. 6 illustrates a radio frequency (RF) antenna 58 that includes an electrical conductor 64 fabricated in the same manner as the conductors 3, 5, 7 and 9, and disposed on a ceramic substrate 60. The electrical conductor 64 may be curvilinear, or it may include a series of straight lines. The electrical conductor 64 could have a wide variety of geometries depending upon the requirements for transmitting and/or receiving RF signals at a predetermined frequency or range of frequencies. The electrical conductor 64 is encapsulated by a layer of insulating glass 62.

Figure 7:
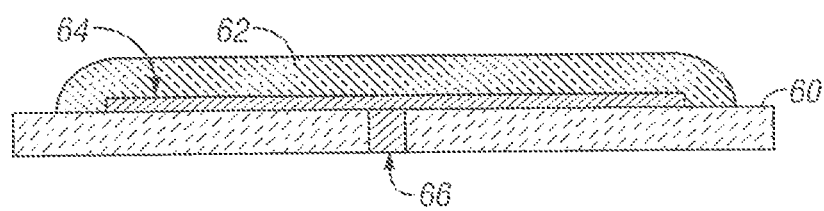
FIG. 7 is a section view of the radio frequency antenna of FIG. 6.

FIG. 7 is a cross sectional view of the antenna of FIG. 6 that illustrates the location of a conductive filled via 66, that provides electrical continuity with the electrical conductor 64. The conductive filled via 66 can be formed in a hole in the ceramic substrate 60 by screen printing a thick film material or by inserting a wire, rivet, or other metallic element since it is covered by the glass insulating layer 62 and therefore need not of itself provide a hermetic seal. The conductive filled via 66 may have a diameter that is larger than the width of the electrical conductor 64. The via 66 may also be located such that it is not precisely centered beneath the electrical conductor 64. In an alternative embodiment of the antenna 58, there may be a second conductive filled via (not illustrated) also providing electrical continuity with the electrical conductor 64, but spaced apart from the first conductive filled via 66, and allowing for an alternative type of antenna.

The present invention also provides a method of fabricating a sensor implantable in the human body for monitoring the level of a biological agent in a bodily fluid. The initial step of our method involves providing a substrate made of a first biocompatible insulating material having a high temperature resistance. An electrically conductive thick film material is then deposited onto the substrate to form at least one un-solidified electrical conductor. After an optional step of drying in a 150° C. oven for about 20 minutes, the next step of our method involves heating the electrically conductive thick film material to a first predetermined temperature below a second predetermined melting temperature thereof, which is sufficient to sinter the metal particles to a high degree. The sintering can occur in a range of temperature that can extend as much as three hundred degrees C. below the second predetermined temperature depending upon the nature of the thick film material. The thick film material is allowed to cool to produce at least one solidified electrical conductor. The solidified electrical conductor has a first porosity which is substantially less than a second porosity that would have resulted from heating the electrically conductive thick film material to temperatures recommended by the manufacturers of the thick film material, or temperatures found in the prior art. At least a portion of the solidified electrical conductor is then coated with a second biocompatible insulating material, except for an exposed region thereof intended for contacting a fluid or other substance to be detected or monitored. The second biocompatible insulating material is preferably a suitable thick film dielectric material.

Variations in our basic method will occur to those skilled in the art including the selection of the various materials, the temperature ranges, cycle times, dwell times, ramp rates and so forth. It is preferable to fire the electrically conductive thick film to drive off the volatile and organic components thereof and sinter the metal particles, before coating the same with the second insulating material, which may then separately be heated to re-flow, melt, fire, harden or otherwise cure the same. The electrically conductive thick film material may first be dried at a relatively low temperature to drive off the volatile components thereof, and then subsequently fired at a high temperature to drive off the remaining organic components and to sinter the metal particles in a manner that ensures reduced porosity thereof.

Figure 8:
FIG. 8 is a cross-sectional scanning electron micrograph of a region encompassing a substrate layer, a fired platinum conductor layer, and a dielectric glass encapsulation layer, where the materials were fired using conventional processes and temperatures.
Figure 9:
FIG. 9 is a close-up view of the platinum conductor layer of FIG. 8, showing a porous structure.
Figure 10:
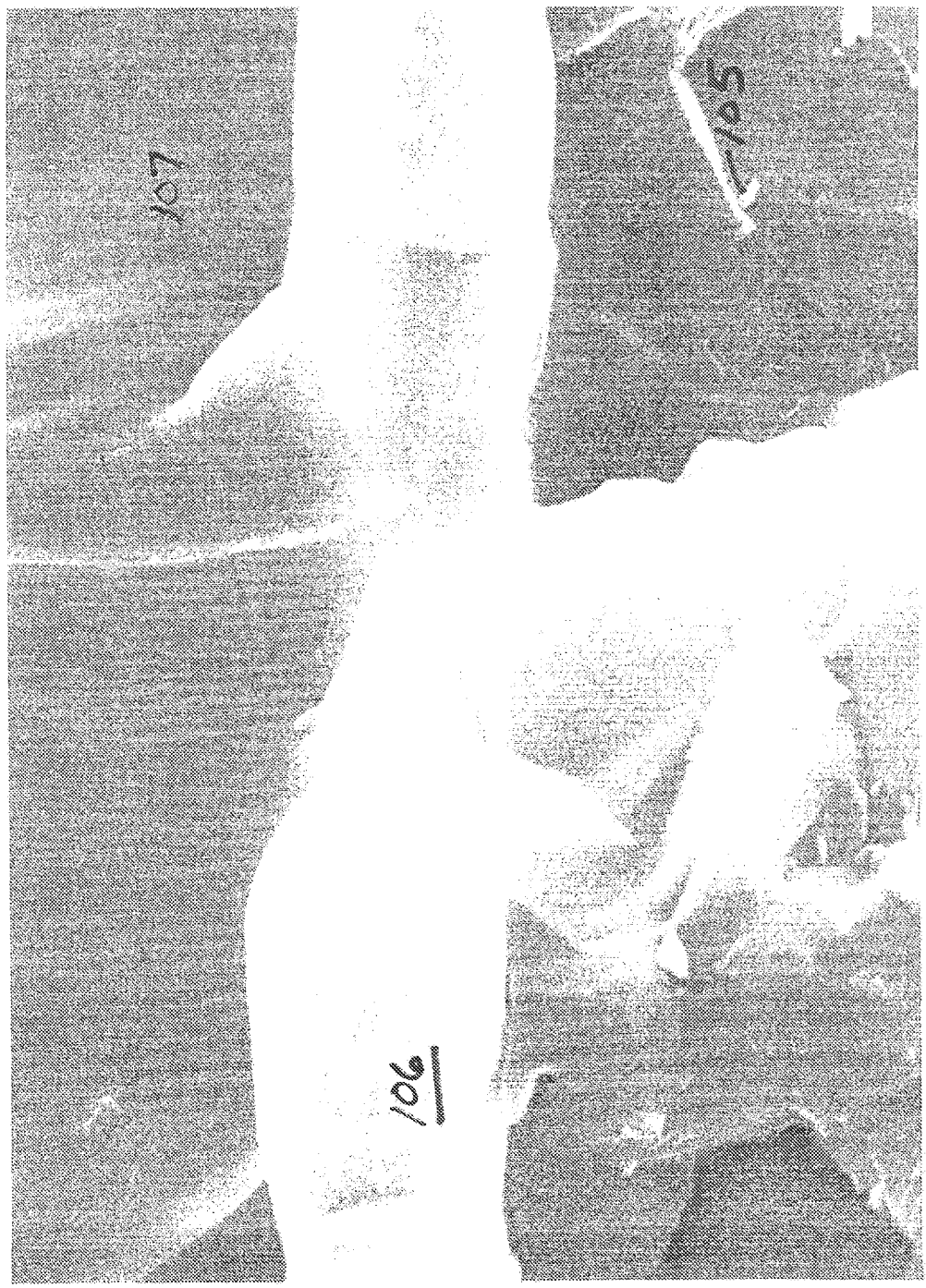
FIG. 10 is a close-up scanning electron micrograph of a platinum conductor layer fabricated in accordance with an embodiment of the present invention.

The beneficial effects of the technique of the present invention on a fired conductor and overlying insulation are shown in FIG. 8, FIG. 9, and FIG. 10. FIG. 8 shows a scanning electron micrograph cross-section of a structure realized using conventional processing methods, as disclosed in the prior art. A temperature-resistant substrate layer 100 is composed of 96% alumina. A conductor layer 101 is composed of thick-film platinum paste, which has been fired at a conventional processing temperature of 1200° C. A glass insulation layer 102 covers the conductor layer. The conductor layer 101 contains numerous pores and voids which are the result of incomplete densification during the conventional 1200° C. firing process. These voids, during the heating process required to fire the glass insulation 102, release trapped gases and produce further voids 103 in the glass insulation, 102. The voids, 103 can, in some circumstances, be large enough to completely disrupt the integrity of the insulation 102, producing a significant defect. FIG. 9 is a higher magnification view of a portion of the platinum conductor layer 101 shown in FIG. 8, and shows one of the voids 104, in the platinum conductor layer 101. FIG. 10 is a scanning electron micrograph cross-section of a structure comprising the same materials shown in FIGS. 8 and 9, but fabricated using the processing techniques of the present invention. A substrate 105 is composed of 96% alumina. A platinum thick film paste has been deposited on the substrate 105, and fired at 1600° C. to produce a dense, void-free conductor layer 106. Glass insulation was subsequently deposited and fired over the platinum conductor 106 to produce the dense, void-free insulation layer 107. In addition to increasing the density of conductor and insulation layers, the method of the present invention also encourages intimate contact between the substrate 105, conductor 106, and insulation 107. Intimacy of contact among these layers is necessary to achieve hermeticity of the structure.

Figure 11:
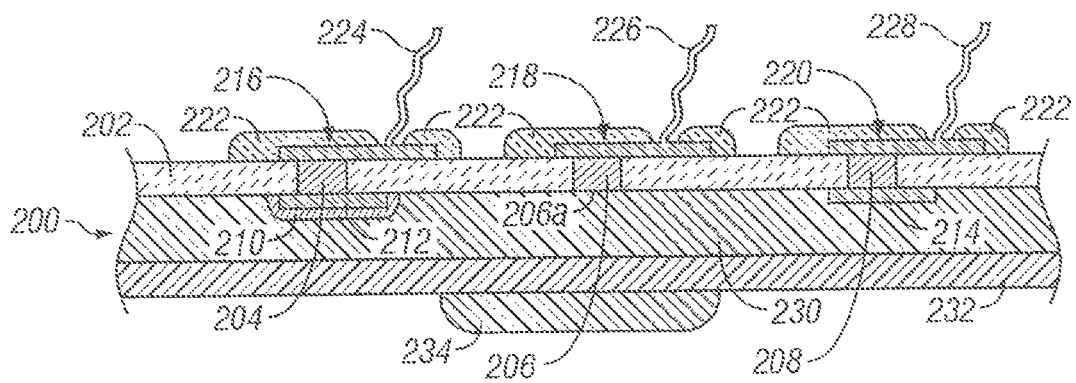
FIG. 11 is a greatly enlarged diagrammatic fragmentary cross-sectional view of an embodiment of a sensor suitable for detecting glucose levels in the human body.

FIG. 11 illustrates the currently preferred embodiment of our invention in the form of an implantable sensor 200 for determining glucose levels in the human body. The sensor 200 includes a ceramic substrate 202 through which three conductive feedthroughs 204, 206 and 208 extend. As described earlier, the feedthroughs 204, 206 and 208 may be provided in the form of wires, rivets or other structures formed by the application and firing of conductive thick film materials inside holes in the ceramic substrate 202. The three feedthroughs 204, 206 and 208 are used to conduct signals from three corresponding electrodes. A working electrode is provided by the exposed face 206a, which may have an increased surface area by a method such as platinizing of the center feedthrough 206. A reference electrode is provided in the form of a layer 210 of silver/silver chloride formed over a conductor 212 formed on top of, and in electrical contact with, the left feedthrough 204. A counter-electrode 214 is spaced a suitable distance from the reference electrode 210. The counter-electrode 214 is provided in the form of a conductor formed on top of, and in electrical contact with, the right feedthrough 208. The feedthroughs 204, 206 and 208 and the conductors 212 and 214 are preferably made of platinum-family metals because of their high temperature resistance, their corrosion resistance and, in the case of the working electrode, their catalytic properties.

On the interior side of the ceramic substrate 202 (FIG. 11) the feedthroughs 204, 206 and 208 are in electrical contact with three conductors 216, 218 and 220, respectively, each similar to the conductors 36 of the FIG. 4 embodiment. The conductors 216, 218 and 220 are each encapsulated in an insulating layer 222 similar to the insulating layer 44 of the FIG. 4 embodiment. Lead wires 224, 226 and 228 are attached to the conductors 216, 218 and 220, respectively, via gaps in the insulating layer 222. The lead wires 224, 226 and 228 electrically connect the three electrodes 210, 206a and 214, respectively, to potentiostat instrumentation (not illustrated). Thus, the conductors 216, 218 and 220 and the insulating layer 222 provide hermetically sealed conductive paths from the lead wires 224, 226 and 228 to the feedthroughs 204, 206 and 208, which connect electrically to the three electrodes 210, 206a and 214, and thus from the interior of the sensor 200 to the exterior thereof.

On the exterior of the sensor 200 (FIG. 11), the three electrodes 210, 206a and 214 are maintained in ionic contact with each other through an electrolyte gel layer 230 that is covered by a polymer membrane 232. Suitable techniques for preparation of an electrolyte gel and polymer membrane are disclosed in U.S. Pat. No. 4,703,756 granted Nov. 3, 1987 to David A. Gough and Joseph Y. Lucisano et al., the entire disclosure of which is hereby incorporated by reference. A glucose-responsive membrane 234, which may be of a composite or laminate construction, affixed over the polymer membrane 232 provides sensitivity of the sensor 200 to glucose levels in the interstitial fluid. Suitable techniques for preparation of the glucose-responsive membrane 234 are disclosed in Provisional Patent Application Pub. No. US 2002/0156355 A1 of David A. Gough published Oct. 24, 2002, the entire disclosure of which is hereby incorporated by reference.

While the sensor 200 of FIG. 11 has three electrodes, this embodiment can be modified by combining the reference electrode 210 and the counter electrode 214. Moreover, while the sensor 200 is particularly suited for detecting glucose levels, its basic structure can be modified to accommodate other electrochemical processes using different types of membranes and coatings to detect other substances.

Example 1

A pattern of Ferro 4082 Vitr-Au-Less high-purity platinum thick film paste is screen printed onto 96% alumina "multistrates." The multistrates each contain nine 0.472-inch-diameter discs, each with 24 five-mil holes, previously formed by laser processing. The platinum paste is printed through a screen that was made with a "traces" pattern and a two-mil-thick emulsion. For each disc, the "traces" pattern consists of twenty-four approximately 10-mil-wide bands, one end of each of which overlaps one of the holes in the disc. A single layer of platinum thick film paste is printed in this pattern using two wet passes of the screen printer squeegee.

The platinum pattern is dried onto the multistrates in an oven at 150° C. for 20 minutes. The multistrates are then individually fired in air at peak temperatures of 1400, 1500, 1600, and 1700° C. for durations of either 10 or 60 minutes, resulting in eight different batches of nine discs each. Photographs of the discs are taken to detail the condition of the fired platinum.

The fired multistrates are then printed with a pattern of ESL 4612-C dielectric thick film paste. The dielectric paste is printed through a screen made with a "dielectric" image and a one-mil-thick emulsion. For each disc in the multistrates, the "dielectric" pattern covers the 24 holes and the adjoining portion of each of the platinum traces, but leaves exposed the other end of each of the platinum traces. This combination of traces, dielectric, and holes in the discs provides a possible leak path from one flat side of the disc to the other, but only if the dielectric-covered portion of the platinum trace is not hermetic. Two layers of dielectric are printed in this pattern using a single wet pass each time. After the first layer of dielectric, the pattern is dried onto the multistrates in an oven at 150° C. for twenty minutes. The multistrates are then fired in air at a peak temperature of 900° C. for a duration of about sixty minutes. The drying and firing are repeated after the second layer of dielectric is printed.

The discs are removed from their multistrates and tested for hermeticity using a Varian Multi-Test 947 helium leak detector, operated and calibrated in accordance with the manufacturer's instructions. Leaks less than $1.0 \times 10^{-8}$ atm cc/s He are considered hermetic in accordance with the military standard, MIL-STD-883E, test condition A4, tracer gas helium (He), fine leak. The testing is accomplished by placing each disc in a custom-made, stainless steel leak-detection fixture which uses butyl rubber O-rings. The disc-and-fixture assembly is then attached to the leak detector, which reaches vacuum pressures of less than ten millitorr. The exterior of the assembly is flooded with industrial grade He gas, and the leak rate is recorded. The following table illustrates the time/peak temperature combinations that leaked and those that were hermetic. The shaded entries were not hermetic. It is important to keep in mind that each disc contains twenty-four separate leak paths, and the paths are evaluated for helium leakage only in a parallel arrangement. Therefore, a leak in any of the twenty-four paths on a single disc would produce a result that would be recorded in the table as a non-hermetic disc.

TABLE I

| Pt Firing Conditions | | Leak Test Results | | | | | |
|---|---|---|---|---|---|---|---|
| Peak Temp (deg. C.) | Duration (min) | Serial # | He Leak (cc/s) | Serial # | He Leak (cc/s) | Serial # | He Leak (cc/s) |
| 1400 | 10 | D171-1 | 4.80E−03 | D171-4 | 3.00E−03 | D171-7 | 5.80E−03 |
|  |  | D171-2 | 5.20E−03 | D171-5 | 4.60E−03 | D171-8 | 3 40E−03 |
|  |  | D171-3 | 4.40E−03 | D171-6 | 6.00E−03 | D171-9 | 1.40E−03 |
| 1400 | 60 | D171-10 | 3.60E−03 | D171-13 | 4.80E−03 | D171-16 | 3.60E−03 |
|  |  | D171-11 | 1.40E−03 | D171-14 | 2.20E−03 | D171-17 | 2.40E−03 |
|  |  | D171-12 | 3.20E−03 | D171-15 | 2.40E−03 | D171-18 | 2.60E−03 |
| 1500 | 10 | D171-19 | 2.80E−03 | D171-22 | 1.40E−03 | D171-25 | 2.00E−03 |
|  |  | D171-20 | 2.80E−03 | D171-23 | 2.20E−03 | D171-26 | 1.00E−03 |
|  |  | D171-21 | 2.20E−03 | D171-24 | 1.80E−03 | D171-27 | 1.20E−03 |
| 1500 | 60 | D171-46 | 2.00E−10 | D171-49 | 2.20E−09 | D171-52 | 1.00E−05 |
|  |  | D171-47 | 1.80E−09 | D171-50 | 8.00E−10 | D171-53 | 140E−05 |
|  |  | D171-48 | 1.60E−05 | D171-51 | 4.00E−09 | D171-54 | 1.40E−05 |
| 1600 | 10 | D171-37 | 5.80E−09 | D171-40 | 3.20E−09 | D171-43 | 1.60E−09 |
|  |  | D171-38 | 3.80E−09 | D171-41 | 2.00E−10 | D171-44 | 1.00E−05 |
|  |  | D171-39 | 4.40E−09 | D171-42 | 3.40E−09 | D171-45 | 1.80E−09 |
| 1600 | 60 | D171-28 | 4.40E−09 | D171-31 | 2.20E−09 | D171-34 | 3.80E−09 |
|  |  | D171-29 | 4.40E−09 | D171-32 | 2.00E−10 | D171-35 | 2.20E−09 |
|  |  | D171-30 | 2.20E−05 | D171-33 | 5.60E−09 | D171-36 | 3.40E−09 |
| 1700 | 10 | D171-55 | 8.00E−10 | D171-58 | 2.00E−10 | D171-61 | 6.00E−10 |
|  |  | D171-56 | 2.00E−10 | D171-59 | 5.60E−09 | D171-62 | 2.00E−10 |
|  |  | D171-57 | 2.00E−10 | D171-60 | 3.60E−09 | D171-63 | 2.40E−09 |
| 1700 | 60 | D171-64 | 4.00E−10 | D171-67 | 6.00E−10 | D171-70 | <1E−10 |
|  |  | D171-65 | — (broke) | D171-68 | <1E−10 | D171-71 | 2.00E−10 |
|  |  | D171-66 | <1E−10 | D171-69 | <1E−10 | D171-72 | <1E−10 |

The results of the helium leak testing indicate that, with a firing duration of sixty minutes, hermeticity may not be reliably achieved below a firing temperature of 150CTC. The reliability of achieving hermeticity is seen to increase with increasing firing temperature above 1500° C. The few instances of non-hermeticity seen in the parts that were fired above 1500° C. were traced to other defects in assembly.

While we have described several embodiments of our invention, it will be understood by those of ordinary skill in the art that our invention can be modified in both arrangement and detail. For example, a source of enzyme such as glucose oxidase (GO) could be added to the sensor adjacent to the detection electrodes in order to catalyze the reaction of glucose and oxygen as is well known in the art. Our sensor can be optimized for detecting various biological agents such as glucose, lactate, cholesterol etc. in various bodily fluids such as interstitial fluid or blood. Integrated circuitry could be formed directly on, or placed on, the ceramic substrate using complementary metal oxide semiconductor (CMOS) or other well-known microelectronic fabrication techniques, and hermetically sealed with the same material that encapsulates the detection electrodes. This circuitry could be separately mounted in the metal case 40 on a different substrate. The circuitry could include a multiplexer and a radio frequency (RF) transceiver that, along with an antenna separately constructed and supported on the substrate or attached to the case 40, could provide a transcutaneous telemetry system for wireless transmission of sensor data to instruments outside the human body and reception of commands to effectuate, for example, monitoring, recording and calibration, as disclosed in the previously mentioned U.S. Pat. No. 4,703,756 of David A. Gough and Joseph Y. Lucisano et al. The sensor could have electrodes of the present invention terminating in three electrodes in the form of a reference electrode, a working electrode and a counter electrode each made of special metals or matrix material and use various impedance increasing and switching techniques to inhibit electrode dissolution, as disclosed in U.S. Pat. No. 5,985,129 granted Nov. 16, 1999 to David A. Gough and Joseph Y. Lucisano, the entire disclosure of which is hereby incorporated by reference. Various membrane structures are preferably used with the electrodes, and even to coat the entire sensor, in order to optimize oxygen independence, diffusional length for the glucose, response times, etc. as taught in U.S. Pat. No. 4,484,987 granted Nov. 27, 1984 to David A. Gough, U.S. Pat. No. 4,650,547 granted Mar. 17, 1987 to David A. Gough, and the aforementioned Provisional Patent Application Pub. No. US 2002/0156355 A1 of David A. Gough, the entire disclosures of which are all hereby incorporated by reference. Presumably the membrane selects only the species of compound or matter intended to interact with the exposed regions of the detection electrodes. Encapsulated conductors utilized as antennas or as elements in an inductive or radiative coupling arrangement are preferably fabricated in a loop pattern, but may also be fabricated in strip, patch, "splatch," dipole, coil, serpentine, or other patterns. Substrates used to realize additional embodiments could have non-planar surfaces, or could also serve multiple purposes. For instance, they could comprise structural members, or could be joined to or form part of a case for an implantable device, in addition to serving as a substrate for the conductor of the present invention. Therefore the protection afforded our invention should only be limited in accordance with the scope of the appended claims.

What is claimed is:
1. A sensor, comprising:
a substrate made of a first insulating material having a high temperature resistance;
at least one conductor disposed over a preselected external surface location on the substrate, wherein the external surface location is planar and disposed on an upper or lower external surface of the substrate, and the at least one conductor is elongated along the external surface location and made from a solidified electrically conductive thick film material which contains particles of a metal selected from the group consisting of platinum, palladium, rhodium, ruthenium, iridium and osmium;
a coating made of a second insulating material formed over at least a portion of the at least one conductor to hermetically seal at least a portion of the at least one conductor;
an exposed distal region of the at least one conductor providing a detection electrode; and
the at least one conductor being sintered by heating to a temperature within a range that extends from below a melting point of the particles of metal to approximately 300° C. below the melting point of the particles of metal and having a reduced porosity that inhibits migration of fluid or constituents thereof through the at least one conductor, wherein the at least one conductor is hermetic along its elongated length.

2. The sensor of claim 1 wherein the first insulating material is selected from the group consisting of ceramic and glass/ceramic combinations.

3. The sensor of claim 2 wherein the ceramic is selected from the group consisting of oxides, carbides, borides, nitrides, and silicides of aluminum, zirconium, beryllium, silicon, titanium, yttrium, and zinc and mixtures thereof.

4. The sensor of claim 1, wherein the second insulating material is selected from the group consisting of glass, ceramic, glass/ceramic combinations, and polymers.

5. The sensor of claim 1 wherein the substrate has a generally planar configuration.

6. The sensor of claim 1 wherein there are at least two conductors that are elongated and parallel.

7. The sensor of claim 1 wherein at least one insulation-testing conductor is formed on the substrate in addition to the at least one conductor, and the coating of the second insulating material hermetically seals at least a portion of the insulation-testing conductor that may come into contact with a fluid.

8. The sensor of claim 1 further comprising a source of glucose oxidase (GO) positioned in operative contact with the detection electrode for catalyzing the reaction of glucose and oxygen.

9. The sensor of claim 1 wherein an exposed proximal region of the at least one conductor provides a contact pad.

10. The sensor of claim 1 wherein an electrical contact connects to the at least one conductor, the contact being selected from the group consisting of a metal wire, sintered metal particles, a sintered mixture of metal and inorganic oxide particles, and a metal plug.

11. A sensor suitable for implanting in living tissue for monitoring the level of a biological agent in a tissue fluid, comprising:
a substrate made of a first biocompatible insulating material having a high temperature resistance selected from the group consisting of ceramic and glass/ceramic combinations;
at least one conductor disposed over a preselected external surface location on the substrate, wherein the external surface location is planar and disposed on an upper or lower external surface of the substrate, and the at least one conductor is elongated along the external surface location and made from an electrically conductive thick film material containing particles of a metal selected from the group consisting of platinum, palladium, rhodium, ruthenium, iridium and osmium;
a coating made of a second biocompatible insulating material selected from the group consisting of glass, ceramic, glass/ceramic combinations, and polymers, and formed over at least a portion of the at least one conductor to hermetically seal at least a portion of the at least one conductor leaving at least one exposed region thereof to provide a detection electrode; and
the at least one conductor being made of metal particles sintered by heating to a temperature within a range that extends from below a melting point of the particles of metal to approximately 300° C. below the melting point of the particles of metal and the at least one conductor having a reduced porosity that inhibits migration of the tissue fluid or any constituents thereof through the at least one conductor, wherein the at least one conductor is hermetic along its elongated length;
whereby instances of sensor failure and/or inaccuracy during implanted operation are minimized.

12. An electrochemical sensor, comprising:
a substrate made of a first insulating material having a high temperature resistance;
at least one conductor disposed over a preselected external surface location on the substrate, wherein the external surface location is planar and disposed on an upper or lower external surface of the substrate, and the at least one conductor is elongated along the external surface location and made from an electrically conductive thick film material containing particles of a metal selected from the group consisting of platinum, palladium, rhodium, ruthenium, iridium and osmium;
a coating made of a second insulating material formed over at least a portion of the at least one conductor to hermetically seal at least a portion of the at least one conductor leaving at least one exposed region to provide a detection electrode; and
the at least one conductor being sintered by heating to a temperature within a range that extends from below a melting point of the particles of metal to approximately 300° C. below the melting point of the particles of metal and having a reduced porosity that inhibits migration of fluid or gaseous diffusion through the at least one conductor, where the at least one conductor is hermetic along its elongated length.

13. A device, a portion of which relies on the conduction of electricity for its function, suitable for implanting in living tissue, which may come into contact with tissue fluid, comprising:
a substrate made of a first biocompatible insulating material having a high temperature resistance;
at least one conductor disposed over a preselected external surface location on the substrate, wherein the external surface location is planar and disposed on an upper or lower external surface of the substrate, and the at least one conductor is elongated along the external surface location and made from a solidified electrically conductive thick film material containing particles of a metal selected from the group consisting of platinum, palladium, rhodium, ruthenium, iridium and osmium;
a coating made from a second biocompatible insulating material formed over at least a portion of the at least one conductor to hermetically seal at least a portion of the at least one conductor;
the at least one conductor being sintered by heating to a temperature within a range that extends from below a melting point of the particles of metal to approximately 300° C. below the melting point of the particles of metal and having a reduced porosity that inhibits migration of the tissue fluid or constituents thereof through the at least one conductor, wherein the at least one conductor is hermetic along its elongated length;

a sealed internal portion of the device containing electrical circuitry; and means for making an electrical connection to the at least one conductor from the exterior of the device.

14. A device as in claim 13 wherein the means for making an external electrical connection comprises a hole in said second biocompatible insulating material adjacent to the at least one conductor.

15. A device as in claim 13 wherein the means for making an external electrical connection comprises a wire.

16. A device as in claim 13 wherein the means for making an external electrical connection comprises an inductive coupling.

17. A device as in claim 13 wherein the means for making an external electrical connection comprises a radiative coupling.

18. A sensor, comprising:

a substrate made of a first insulating material having a high temperature resistance;

at least one conductor disposed over a preselected external surface location on the substrate, wherein the external surface location is planar and disposed on an upper or lower external surface of the substrate, and the at least one conductor is elongated along the external surface location and made from a solidified electrically conductive thick film material containing particles of a metal selected from the group consisting of platinum, palladium, rhodium, ruthenium, iridium and osmium;

a coating made of a second insulating material formed over at least a portion of the at least one conductor to hermetically seal at least a portion of the at least one conductor;

a conductive filled via formed in an aperture in the substrate and in electrical contact with the at least one conductor; and the at least one conductor being sintered by heating to a temperature within a range that extends from below a melting point of the particles of metal to approximately 300° C. below the melting point of the particles of metal and having a reduced porosity that inhibits migration of fluid or constituents thereof through the at least one conductor, wherein the at least one conductor is hermetic along its elongated length.

* * * * *